US008101361B2

(12) United States Patent
Saavedra et al.

(10) Patent No.: US 8,101,361 B2
(45) Date of Patent: Jan. 24, 2012

(54) MARKERS FOR DIAGNOSIS OF PULMONARY INFLAMMATION AND METHODS RELATED THERETO

(75) Inventors: Milene Saavedra, Denver, CO (US); Jerry Nick, Denver, CO (US)

(73) Assignee: National Jewish Health, Denver, CO (US)

( * ) Notice: Subject to any disclaimer, the term of this patent is extended or adjusted under 35 U.S.C. 154(b) by 65 days.

(21) Appl. No.: 12/401,381

(22) Filed: Mar. 10, 2009

(65) Prior Publication Data
US 2009/0233300 A1 Sep. 17, 2009

Related U.S. Application Data

(60) Provisional application No. 61/035,227, filed on Mar. 10, 2008.

(51) Int. Cl.
*C12Q 1/68* (2006.01)
*C07H 21/02* (2006.01)
*C07H 21/04* (2006.01)
*C07K 14/435* (2006.01)

(52) U.S. Cl. ........ 435/6.11; 435/6.1; 435/6.17; 435/7.1; 536/23.5; 530/350; 530/351

(58) Field of Classification Search .................. None
See application file for complete search history.

(56) References Cited

U.S. PATENT DOCUMENTS

| 2005/0113345 | A1 | 5/2005 | Chow et al. | |
| 2005/0214871 | A1 | 9/2005 | Boon et al. | |
| 2008/0226645 | A1* | 9/2008 | O'Toole et al. | 424/139.1 |
| 2009/0202514 | A1 | 8/2009 | Yoneyama et al. | |

FOREIGN PATENT DOCUMENTS

| WO | WO 2004/010139 | 1/2004 |
| WO | WO 2008/023446 | 2/2008 |

OTHER PUBLICATIONS

Liu et al. Clinical Immunology. 2004. 112: 225-230.*
Coleman. Drug Discovery Today. 2003. 8: 233-235.*
Saetre et al. Molecular Brain Research. 2004. 126: 198-206.*
Palmer et al. BMC Genomics. 2006. 7:115.*
Hansel et al. J. Lab. Clin. Med. 2005. 263-274.*
Min et al. BMC Genomics. 2010. 11:96.*
Gupta et al. AAPS PharmSci 3 Meeting Abstracts. 2001. 4, Suppl #M2311.*
Woodruff et al. PNAS. Sep. 26, 2007. 104: 15858-18563.*
Kowal et al., "Differential expression of monocyte CD163 in single- and dual-asthmatic responders during allergen-induced bronchoconstriction," Clinical and Experimental Allergy, 2006, vol. 36, No. 12, 1584-1591.
Pons et al., "Expression of Toll-like receptor 2 is up-regulated in monocytes from patients with chronic obstructive pulmonary disease," Respiratory Research. 2006, vol. 7, No. 64, pp. 1-9.
Redecke et al., "Cutting Edge: activation of Toll-like receptor 2 induces a Th2 immune response and promotes experimental asthma," The Journal of Immunology, 2004, vol. 172, No. 5, pp. 2739-2743.
International Search Report for International (PCT) Application No. PCT/US2009/036670, mailed Oct. 15, 2009.
Written Opinion for International (PCT) Application No. PCT/US2009/036670, mailed Oct. 15, 2009.
Cunningham et al., "Duration of Effect of Intravenous Antibiotics on Spriometry and Sputum Cytokines in Children with Cystic Fibrosis", Pediatric Pulmonology 36:43-48 (2003).
Hubeau et al., "Quantitative analysis of inflammatory cells infiltrating the cystic fibrosis airway mucosa", Clin Exp Immunol;124:69-76, 2001.
Nixon et al., "Circulating Immunoreactive Interleukin-6 in Cystic Fibrosis", Am J Respir Crit Care Med, vol. 157, pp. 1764-1769, 1998.
Ordoñez et al., "Inflammatory and Microbiologic Markers in Induced Sputum after Intravenous Antibiotics in Cystic Fibrosis", American Journal of Respiratory and Critical Care Medicine, vol. 168, pp. 1471-1475, 2003.
Ramilo et al., "Gene expression patterns in blood leukocytes discriminate patients with acute infections", Blood, 109:2066-2077, 2007.
Reix et al., "Cytokine pattern in cystic fibrosis patients during antibiotic therapy and gene therapy using adenoviral vector", European Cytokine Network, No. 3, vol. 13, 324-30, Sep. 2002, articles originaux.
Saavedra et al., "Circulating RNA Transcripts Identify Therapeutic Response in Cystic Fibrosis Lung Disease", American Journal of Respiratory and Critical Care Medicine, vol. 178, pp. 929-938, 2008.
Weiss et al., "Soluble CD163: An age-dependent, anti-inflammatory biomarker predicting outcome in sepsis", Crit Care Med; No. 10, vol. 34, pp. 2682-2683, 2006.
Wolter et al., "Cytokines and Inflammatory Mediators Do Not Indicate Acute Infection in Cystic Fibrosis", Clinical and Diagnostic Laboratory Immunology, p. 260-265, Mar. 1999.
Wu et al., "Toll-like Receptor 2 Down-regulation in Established Mouse Allergic Lungs Contributes to Decreased Mycoplasma Clearance", Am J Respir Crit Care Med vol. 1777, pp. 720-729, 2008.
International Preliminary Report on Patentability for Application No. PCT/US2009/036670, mailed Sep. 23, 2010.

* cited by examiner

*Primary Examiner* — Carla Myers
(74) *Attorney, Agent, or Firm* — Sheridan Ross P.C.

(57) ABSTRACT

The present invention is related to the novel discovery of a number of genes that were identified as systemic markers of pulmonary inflammation. This discovery allows for development of a novel tool for reliable, rapid and efficient assessment of therapeutic responses and enables design of novel therapies targeted against diseases associated with pulmonary inflammation. In one embodiment, the present invention allows quantification of therapeutic response in patients who have a disease associated with pulmonary inflammation. In preferred embodiments, the genes are CD64, ADAM9, CD36, IL32, HPSE, PLXND1, HCA112, CSPG2, TLR2, and CD163.

5 Claims, 6 Drawing Sheets

MARKERS FOR DIAGNOSIS OF PULMONARY INFLAMMATION AND METHODS RELATED THERETO

CROSS REFERENCE TO RELATED APPLICATIONS

The present application claims the benefit of Provisional Application Ser. No. 61/035,227, filed on Mar. 10, 2008, the entire contents of which are hereby incorporated by reference.

GOVERNMENT SUPPORT

This invention was supported in part with funding provided by NIH Grant No. K08HL74512 and HL090991 awarded by the National Institutes of Health. The government has certain rights to this invention.

FIELD OF THE INVENTION

The field of the present invention is identification of genetic markers for assessing therapeutic responses in diseases associated with pulmonary inflammation.

BACKGROUND

Cystic fibrosis (CF) is the most common lethal inherited disease in the western world. While life expectancies have increased to nearly 40 years, respiratory failure still accounts for >80% of deaths from the disease, usually in young adults in the third or fourth decade of life. The triad of airway obstruction with mucus, chronic endobronchial infection with pathogens such as *Pseudomonas aeruginosa*, and severe airway inflammation, are the major pathogenic factors in CF lung disease (Konstan, 1998, *Clin Chest Med* 19(3):505-13, vi). Given the shortage of solid organs for transplantation in end stage lung disease, there is a critical need for effective anti-microbial and anti-inflammatory therapies to mitigate progression of disease in this young population.

However, the rendering of rapid and efficient clinical trials in CF and other diseases associated with airway inflammation, is hampered, in part, by the lack of sensitive measures of treatment response. Currently, spirometry is the most common pulmonary function test for measuring lung function. Specifically, Forced Expiratory Volume in 1 second or $FEV_1$ is the established standard for assessing pulmonary treatment response. When $FEV_1$ measurements are decreased, treatment is initiated. Following two to three weeks of IV antibiotic therapy, $FEV_1$ measurements are typically repeated as a quantitative measure of clinical response. Similarly, $FEV_1$ measurements are utilized as the gold standard measurement for treatment response in clinical trials.

Airway remodeling, driven by inflammatory cells, most directly impacts progressive decline in lung function, and ultimately survival in CF. While novel anti-inflammatory therapies seek to target this decline, fibrosis and remodeling occur slowly and progressively, and may not be detected in a typical month-long Phase 2 trial. Thus, a beneficial effect of an anti-inflammatory treatment, which slows decline in lung function via reduced fibrosis and remodeling, could be missed with monitoring of lung function by FEV1 alone.

At present, there are no known reliable and sensitive molecular markers which can be used to quantify pulmonary inflammation and assess therapeutic responses against diseases associated with such inflammation. Thus, there exists a need for development of reliable and sensitive markers of airway or pulmonary inflammation that would allow testing of therapeutics against such diseases.

SUMMARY OF THE INVENTION

In one embodiment, the present invention comprises a method for assessing response to a treatment of a disease that is associated with pulmonary inflammation in a subject, comprising the steps of detecting the expression of one or more genes selected from the group consisting of CD64, ADAM9, CD36, IL32, HPSE, PLXND1, HCA112, CSPG2, TLR2, and CD163 in a sample taken from the subject before administering the treatment; detecting the expression of one or more genes selected from the group consisting of CD64, ADAM9, CD36, IL32, HPSE, PLXND1, HCA112, CSPG2, TLR2, and CD163 in a sample taken from the subject after administering the treatment; and comparing the level of the expression of the genes from step (a) in the sample taken from the subject before administering the treatment to the level of the expression of the genes from step (b) in the sample taken from the subject after administering the treatment. In preferred embodiments, the present invention comprises detecting the expression of one or more genes from the group consisting of CD64, ADAM9, CD36 and TLR2.

In some embodiments, the present invention further comprises the step of measuring $FEV_1$ in the subject before and after administering the treatment.

In some embodiments, the sample taken from the subject is blood, sputum, bronchioalveolar lavage or urine. In some embodiments, the sample comprises cells selected from the group consisting of: leukocytes, lymphocytes, monocytes, basophils, and eosinophils.

In some embodiments, the disease associated with the pulmonary inflammation is selected from the group consisting of cystic fibrosis, asthma, chronic pulmonary obstructive disease, emphysema, interstitial lung disease, bronchitis, acute respiratory distress syndrome, and pneumonia. In a preferred embodiment, the disease is cystic fibrosis lung disease.

In some embodiments, detecting the expression of genes comprises detection of RNA transcripts of the gene. In some embodiments, detecting the expression of genes comprises detection of the protein encoded by the gene.

In another embodiment, the present invention comprises a method to identify agents that inhibit the progression of a disease that is associated with pulmonary inflammation, comprising identifying agents that alter the expression or activity of one or more genes selected from the group consisting of CD64, ADAM9, CD36, IL32, HPSE, PLXND1, HCA112, CSPG2, TLR2, and CD163. In some embodiments, the disease associated with the pulmonary inflammation is selected from the group consisting of cystic fibrosis, asthma, chronic pulmonary obstructive disease, emphysema, interstitial lung disease, bronchitis, acute respiratory distress syndrome, and pneumonia. In a preferred embodiment, the disease is cystic fibrosis lung disease.

BRIEF DESCRIPTION OF THE DRAWINGS

FIGS. 4A and 4B show the Receiver-operating-characteristic ("ROC") curves of gene combinations and $FEV_1$. ROC curves depict the fraction of true positive (Sensitivity) and false positive (1 minus specificity) values plotted for RNA transcripts and $FEV_1$% predicted. A perfect test is indicated by AUC=1. A test with no discriminatory value has an AUC=0.50.

DETAILED DESCRIPTION

The present invention relates to novel methods for assessing therapeutic responses in the treatment of a disease that is associated with pulmonary inflammation. These methods are based on the discovery of gene biomarkers whose expression patterns correlate with resolution of pulmonary infection and inflammation. The markers of the present invention represent a novel noninvasive tool to quantify therapeutic responses and to predict resolution of pulmonary exacerbations. The methods of the present invention provide greater sensitivity, specificity and discriminatory capacity than the existing methods that are based on measurements of $FEV_1$ alone and when used in conjunction with measurements of $FEV_1$ enhance the predictive power of $FEV_1$.

This is believed to be the first report to utilize gene expression patterns to assess response to therapy in a disease involving pulmonary inflammation. The terms pulmonary inflammation and airway inflammation are synonymous and are used interchangeably in this application. As described herein, the gene expression changes demonstrated reproducibility across two patient groups and discriminatory capacity to differentiate between acutely ill and subsequently treated patients.

Furthermore, the regression model described herein demonstrated that the information related to changes in gene expression add meaningful diagnostic information to $FEV_1$ in assessing treatment response in acute pulmonary exacerbations. The independent, significant explanatory power contributed by these genes demonstrates that gene expression values from the CF therapeutic signature enhance the predictive discriminating value of $FEV_1$ alone.

More specifically, as described herein, the present invention comprises a group of ten genes (CD64, ADAM9, CD36, IL32, HPSE, PLXND1, HCA112, CSPG2, TLR2, and CD163) whose expression patterns were found to correlate with resolution of pulmonary infection and inflammation in cystic fibrosis (CF) lung disease. The list of these genes is shown in Table 3b. Seven of the 10 genes and the proteins they encode (IL32, HPSE, ADAM9, PLXND1, HCA112, CSPG2, and CD163) have not previously been linked to CF lung disease. It is noted that these genes are not specific to CF and have varying roles in other conditions characterized by pathologic pulmonary inflammation, including without limitation, cystic fibrosis, asthma, chronic obstructive pulmonary disease, emphysema, interstitial lung disease, bronchitis, acute respiratory distress syndrome and pneumonia (Wu et al., 2008, Am J Respir Crit Care Med 177(7):720-9; Moller et al., 2006, Crit Care Med 34(10):2561-6). The fact that these genes encode for proteins implicated in inflammatory processes, lends biologic plausibility to naming them as potential markers of resolution of CF airway infection and inflammation, as well as other diseases associated with airway infection and inflammation.

As a group, these genes represent functions of immune recognition and response, phagocytosis, and matrix degradation. TLR2 represents a central pattern recognition receptor for the innate response against bacterial infection. IL-32 is a newly described TNF-inducible intracellular cytokine (Kim et al., 2005, *Immunity* 22(1):131-42). An inducer of proinflammatory cytokines, IL-32 induces blood monocyte differentiation to macrophages, with subsequent phagocytic activity for live bacteria (Netea et al., 2008, Proc Natl Acad Sci U S A 105(9):3515-20). Expression of IL-32 by inflamed luminal epithelia, may facilitate differentiation of blood monocytes infiltrating infected lung (Kim et al., 2005, Immunity 22(1):131-42). Three surface receptor genes participate in phagocytosis. CD64, or FcγRIA, mediates receptor mediated endocytosis of IgG-antigen complexes in macrophages (Rodrigo et al., 2006, *J Virol* 80(20):10128-3). CD36, a scavenger receptor, mediates macrophage uptake of oxidized LDL, as well as serving as a surface receptor for thrombospondin-1 (Kwok et al., 2006, *Am J Physiol Endocrinol Metab.*; Ferreira et al., 2006, *Atherosclerosis*; Doyen et al., 2003, *J Exp Med* 198(8):1277-83). CD163 serves as a macrophage cell surface hemoglobin scavenger receptor, and was recently shown to be highly predictive of mortality in pneumococcal bacteremia (Moller et al., 2006, *Crit Care Med* 34(10):2561-6; Weiss and Schneider, 2006, *Crit Care Med* 34(10):2682-3). Degradative enzymes, including heparanase, ADAM9 and versican, facilitate extravasation of leukocytes to inflamed tissues. In persistent airway inflammation, this process may culminate in marked and irreversible structural injury to lung parenchyma, by modification of extracellular matrix architecture (Vaday and Lider, 2000, *J Leukoc Biol* 67(2):149-59).

The study described herein was designed to measure markers that change with aggressive treatment of a pulmonary exacerbation, the current best therapy for reduction of acute increases in airway infection and inflammation in lung diseases. This design had several advantages. First, the design closely paralleled a clinical trial sequence, in which a treatment would be tested for its effect on decreasing inflammation. Second, the gene signature was not pathogen limited. The patient populations used in this study suffered from infection with a representative variety of bacterial pathogens. When patients were treated for pulmonary exacerbations, expression of most of the candidate genes more closely resembled the normal controls (FIGS. 2A and B), supporting biological roles of these genes as markers of decreased infection and inflammation. Furthermore, half the genes were specific for exacerbation amongst CF patients, meaning values differed significantly prior to treatment versus stable CF patients, but not following treatment compared to stable CF patients. This included the three genes (CD64, ADAM9, and CD36) which were most highly diagnostic of therapeutic response. One of the genes which added significant explanatory power to the regression model in both patient groups, ADAM9, was highly representative of immediate post-exacerbation transcriptional changes, since its post-exacerbation expression remained significantly different from both normal and stable CF controls.

Simultaneous measurements of respiratory physiology and plasma markers allowed for statistical comparisons of multiple outcomes measures. The significant correlation of over half of the genes in the CF therapeutic signature with changes in CRP, a well characterized serum marker of inflammation, in addition to correlations to neutrophil counts, further strengthened the association of these genes with inflammatory processes.

The identification of biomarkers has more immediate clinical implications for several large sub-populations of CF patients. In children, airway infection and inflammation can occur as early as four weeks of age (Khan et al., 1995, *Am J Respir Crit Care Med* 151(4):1075-82). CT radiographic studies have demonstrated considerable bronchiectasis and parenchymal abnormalities in children with normal lung function (de Jong et al., *Eur Respir J* 23(1):93-7). Sensitive markers allow for a personalized strategy of anti-infectious and anti-inflammatory treatment in young children, with the ability to rapidly monitor outcomes from these interventions. Conversely, in patients with severe lung destruction and multiple antibiotic drug resistant organisms, assessment of response to a particular treatment is often difficult, given day-to-day variability in disease and the degree of irreversibility in airway damage. A sensitive measure of leukocyte activities can be used to gauge response to therapeutics when clinical response lags far behind.

In one embodiment, the present invention comprises a method to assess response to a treatment of a disease that is associated with pulmonary inflammation in a subject. The method includes detecting the expression of one or more genes selected from the group consisting of CD64, ADAM9, CD36, IL32, HPSE, PLXND1, HCA112, CSPG2, TLR2, and CD163 in a sample taken from the subject before administering the treatment. The method also includes the step of detecting the expression of the selected genes in the sample taken from the subject after administering the treatment. The method also includes comparing the expression levels of the genes before administering the treatment to the expression levels after administering the treatment. In preferred embodiments, the method includes detecting the expression of one or more genes selected from CD64, ADAM9, CD36 and TLR2.

In some embodiments, the method of the present invention further comprises measuring $FEV_1$ in the subject.

The methods of the present invention can be used to assess therapeutic responses in the treatment of any disease that is associated with pulmonary inflammation. The diseases contemplated herein include, without limitation, cystic fibrosis, asthma, chronic obstructive pulmonary disease, emphysema, interstitial lung disease, bronchitis, acute respiratory distress syndrome and pneumonia. In a preferred embodiment, the disease is cystic fibrosis.

A patient sample can include any bodily fluid or tissue from a patient that may contain the RNA or protein encoded by the genes contemplated here. The term "sample" or "patient sample" can be used generally to refer to a sample of any type which contains products that are to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells that are preferably evaluated. Cells can be obtained, for example, by scraping of a tissue, processing of a tissue sample to release individual cells, or isolation from a bodily fluid.

In some embodiments, the sample may comprise blood, sputum, bronchioalveolar lavage or urine. In a preferred embodiment, the patient sample comprises blood.

In some embodiments the sample may comprise Peripheral Blood Mononuclear Cells (PBMCs), leukocytes, monocytes, lymphocytes, basophils, or eosinophils.

A systemic marker of lung inflammation has many advantages, as blood can be obtained from subjects of any age and disease severity, and may reflect the status of inflammation throughout the lung, rather than one segment. This analysis is sensitive, inexpensive, and obtained from tissue that is easily accessible in pediatric and adult populations, and has the potential to be performed in a clinical laboratory.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not. This can include determining whether the gene expression is upregulated as compared to a control, downregulated as compared to a control, or unchanged as compared to a control. Therefore, the step of detecting expression does not require that expression of the gene actually is upregulated or downregulated, but rather, can also include detecting that the expression of the gene has not changed (i.e., detecting no expression of the gene or no change in expression of the gene).

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding the gene on any of a variety of surfaces; in situ hybridization; and detection of a reporter gene.

Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, *Anal. Biochem.* 212:457; Schuster et al., 1993, *Nature* 365:343). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR). A preferred method is an immunoassay, wherein an $A_{2A}$-specific antibody (an antibody that selectively binds to $A_{2A}$) is used to detect the expression on tumor cells.

A patient sample can include any bodily fluid or tissue from a patient that may contain tumor cells or proteins of tumor cells. More specifically, according to the present invention, the term "test sample" or "patient sample" can be used generally to refer to a sample of any type which contains cells or products that have been secreted from cells to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells that are preferably evaluated. Cells can be obtained, for example, by scraping of a tissue, processing of a tissue sample to release individual cells, or isolation from a bodily fluid.

In another embodiment, the present invention includes a method to identify agents that inhibit the progression of a disease that is associated with pulmonary inflammation, comprising identifying agents that alter the expression or activity of one or more genes selected from the group consisting of CD64, ADAM9, CD36, IL32, HPSE, PLXND1, HCA112, CSPG2, TLR2, and CD163. The diseases contemplated herein include, without limitation, cystic fibrosis, asthma, chronic obstructive pulmonary disease, emphysema, interstitial lung disease, bronchitis, acute respiratory distress syndrome and pneumonia. In a preferred embodiment, the disease is cystic fibrosis.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Example 1

This example illustrates the overall design and step-wise execution of the study described herein.

Figure 1:
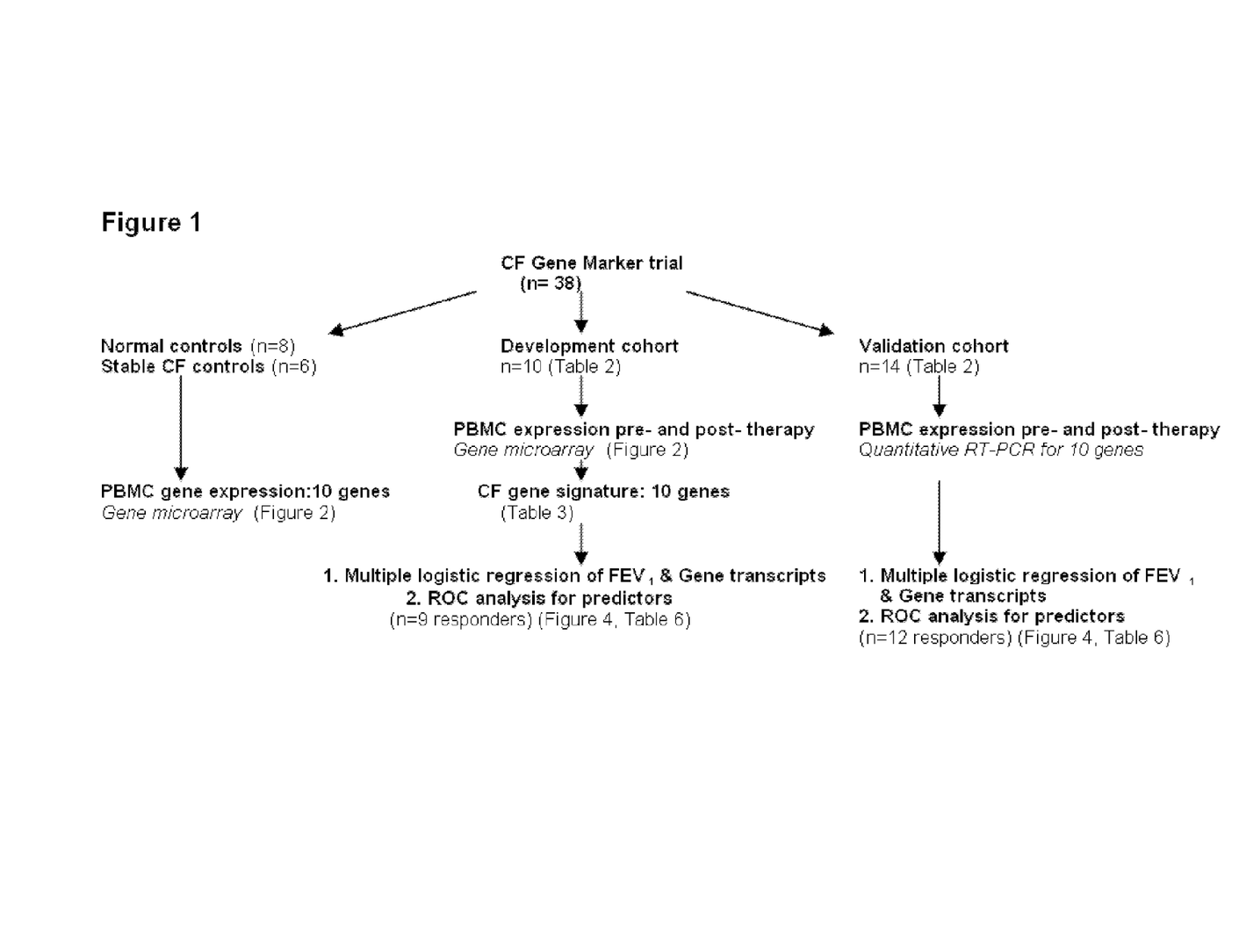
FIG. 1 shows a schematic diagram of the design and execution of the study.

The design of the study is shown in FIG. 1. Peripheral blood mononuclear cells (PBMCs) were isolated from 10 CF patients in the Development Cohort with acute pulmonary exacerbations before and after therapy, as well as healthy non-CF control subjects and stable CF patients matched in age and sex to the patients of Development Cohort. Gene expression profiling was performed by utilizing gene microarray technique to identify genes whose expression significantly changed with treatment. Thus, candidate gene markers, differentially regulated before and after antibiotic therapy were identified. These genes were independently confirmed in the same set of samples, utilizing quantitative RT-PCR.

Further, these markers were tested for their ability to classify therapeutic response in an independent Validation Cohort of 14 acutely ill CF patients, utilizing reverse transcription-PCR amplification technique. The gene expression data from patients who responded to therapy from development and validation cohorts were subjected to statistically analyzed using methods of multiple logistic regression/receiver operating characteristic (ROC) analysis.

Table 1 summarizes measurement distributions performed for all 24 CF patient samples, including 10 from the Development Cohort and 14 from the Validation Cohort.

TABLE 1

Analysis performed on CF patient samples in development and validation cohorts

| Patient | PBMC gene microarray | Quantitative RT-PCR | Plasma cytokine measurements | FEV1 | CRP | Logistic regression model |
|---------|----------------------|---------------------|------------------------------|------|-----|---------------------------|
| 1   | x |   | x | x | x | x |
| 2   | x |   | x | x | x | x |
| 3   | x | x | x | x | x | x |
| 4   | x | x | x | x | x | x |
| 5   | x | x | x | x | x | x |
| 6   | x | x | x | x | x | x |
| 7   | x | x | x | x | x | x |
| 8   | x | x | x | x | x | x |
| 9   | x |   | x | x | x | non-responder |
| 10  | x |   | x | x | x | x |
| V11 |   | x |   | x |   | non-responder |
| V12 |   | x |   | x |   | x |
| V13 |   | x |   | x |   | x |
| V14 |   | x |   | x |   | x |
| V15 |   | x |   | x |   | x |
| V16 |   | x |   | x |   | x |
| V17 |   | x |   | x |   | x |
| V18 |   | x |   | x |   | non-responder |
| V19 |   | x |   | x |   | x |
| V20 |   | x |   | x |   | x |
| V21 |   | x |   | x |   | x |
| V22 |   | x |   | x |   | x |
| V23 |   | x |   | x |   | x |
| V24 |   | x |   | x |   | x |

*V indicates validation cohort population
Nonresponders were not included in logistic regression model Example 2

This Example describes the initial study performed with patients in the Development Cohort for identification of the genetic markers.

Patient recruitment was done as follows. Subjects >18 years of age with CF (based on sweat chloride testing and genotype) were enrolled at the time of admission or home IV antibiotic initiation for a clinically diagnosed pulmonary exacerbation at a large Cystic Fibrosis Foundation accredited adult CF clinic, following obtainment of informed consent from the study subject. All study participants were monitored by the National Jewish Health and University of Colorado Institutional Review Boards. Patients identified for enrollment met CF Foundation Clinical Practice Guidelines of at least 3 of 11 criteria for an acute pulmonary exacerbation (Foundation, C. F. Clinical Practice Guidelines for Cystic Fibrosis).

All patients were treated with at least 2 antibiotics targeting their specific bacterial pathogens for a minimum of 2 weeks and a maximum of three weeks. The study design utilized within subject comparisons, such that each study subject served as their own control, following treatment with antibiotics. Blood was drawn at the initiation (±2 days) and the completion (±1 week) of intravenous antibiotic therapy. At each timepoint, the following were collected or measured: 1) blood for PBMC isolation 2) sputum for microbiologic analysis 3) simple spirometry for $FEV_1$ determination according to American Thoracic Society guidelines and 4) plasma isolation from the blood preparation for cytokine measurements.

The baseline demographics, severity of airflow limitation, genotype, and sputum microbiology for the development and validation cohorts are shown in Table 2. As shown in table 2, both groups had moderate to severe airways disease by ATS criteria, based on $FEV_1\%$ predicted measured at the completion of IV antibiotic therapy (Pellegrino et al., 2005, Eur Respir J 26(5):948-68). Ninety percent of patients in both groups grew Pseudomonas aeruginosa on sputum culture at the time of therapy. Staphylococcus aureus was commonly isolated in both groups, though only 1 strain was methicillin resistant. While no patients were treated with steroids in the development cohort, over half of the validation cohort received steroids (p=0.002). The median pre-treatment $FEV_1\%$ was lower in the validation group (p=0.04); however, post-treatment $FEV_1\%$ predicted did not significantly differ between groups. All patients exhibited $FEV_1$ increases at the conclusion of therapy except for one single patient in the development cohort, whose $FEV_1\%$ predicted declined by 26% after therapy. This patient concomitantly suffered a severe flare of CF-related arthritis at the end of her antibiotic therapy. Given the drop in $FEV_1$, this patient was considered a non-responder, and her gene copy changes were not utilized in the regression analyses for genes with $FEV_1$.

TABLE 2

Base-line characteristics of study population.

| Characteristic | Development group (n = 10) | Validation group (n = 14) |
|---|---|---|
| Age* (mean) - yr | 26 ± 5.7 | 27 ± 3 |
| Gender - no. (%) | | |
| Male | 3 (30) | 9 (64) |
| Female | 7 (70) | 5 (42) |
| Genotype - no. (%) | | |
| DF508/DF508 | 8 (80) | 9 (64) |
| Other | 2 (20) | 5 (36) |
| FEV1* (median % predicted) | | |
| Pre | 44 ± 19 | 31.5 ± 18‡ |
| Post | 51 ± 18 | 44 ± 20 |
| Sputum culture - no. (%) | | |
| Pseudomonas aeruginosa | 9 (90) | 13 (93) |
| Staphylococcus aureus (methicillin sensitive) | 7 (70) | 8 (57) |
| Staphylococcus aureus (methicillin resistant) | 1 (10) | 0 |
| Other (B. cepacia, A. xylosoxidans, A. fumigatus) | 1 (10) | 4 (29) |
| Systemic antibiotic therapy- no. (%) | | |
| APAG + 4th gen Ceph or Carbapenem or Monobactam** | 7 (70) | 10 (71) |
| Other combination^ | 3 (30) | 4 (29) |
| Systemic steroid use - no (%) | 0 | 8 (57)‡ |
| CFRD - no. (%) | 4 (40) | 5 (36) |

*Plus-minus values indicate ± SD.
**APAG represents anti-pseudomonal aminoglycoside, and 4th gen Ceph represents fourth generation cephalosporin
^Other therapy includes vancomycin, nafcillin, cefazolin, levofloxacin and carbapenem/monobactam combinations
‡p < 0.05
B. cepacia indicates Burkholderia cepacia
A. xylosoxidans indicates Alcaligenes xylosoxidans
A. fumigatus indicates Aspergillus fumigatus
CFRD represents CF- related diabetes mellitus as diagnosed by CF Foundation guidelines PBMC isolation was performed as follows. Four ml of peripheral blood was collected into sodium citrate tubes (BD Vacutainer® CPT™, BD Biosciences, Franklin Lakes, N.J.) utilizing a Ficoll Hypaque density gradient. PBMC's were isolated via density gradient centrifugation (1650 RCF, 30 minutes, 18° C.). Furthermore, cytospins with H&E staining verified that all cells from which RNA was extracted were mononuclear and fewer than 1% neutrophils were identified from the interphase.

The RNA was isolated by Trizol method, and purified using the Rneasy Mini Kit (Qiagen) according to manufacturer's protocol. cDNA was reverse transcribed from total RNA using the Superscript II Reverse Transcriptase™ Kit (Invitrogen, Carlsbad, Calif.). Complete blood counts were done to quantify cell numbers. Additionally, cell counts were done after each isolation in order to insure that differences in transcript abundance were not due to differences in cell counts, PBMC's were counted at the time of each isolation, and absolute numbers between timepoints evaluated by paired t tests.

Microarray hybridization and data analysis was performed as follows. PBMC RNA isolated from the development cohort, containing 10 patients representing 10 pulmonary exacerbations, was utilized for microarray analysis, in order to identify PBMC transcriptional changes before and after antibiotic therapy. All raw microarray data is available on the NCBI Gene Expression Omnibus Database. Prior to microarray, all RNA was evaluated with an Agilent 2100 Bioanalyzer to confirm high grade RNA quality. PBMC gene expression analysis was performed with Hu133 Plus 2.0 gene chips. Samples were prepared for Affymetrix arrays using 2.5 µg of total RNA. First and second strand complimentary DNA was synthesized using standard techniques. Biotin-labeled antisense complimentary RNA was produced by an in vitro transcription reaction. Target hybridization, washing, staining, and scanning probe arrays were done following manufacturer's protocol as described in the Affymetrix GeneChip Expression Analysis Manual. Affymetrix CEL files were loaded into dChip 2005 array analysis software (Li C, Wong W H 2001), normalized to median brightness, and expression modeled using the perfect match/mismatch (PM/MM) algorithm.

Beginning with microarrays containing over 35,000 sequences from 10 patients before and after antibiotic treatment, sequences assigned to known genes with a minimum expression threshold (Affymetrix "present call") were focused upon. The study design utilized "within subject comparisons", such that each study subject served as their own control. From these genes, differentially expressed genes were identified in pairwise comparisons between pre- and post-treatment groups, using a non-parametric Wilcoxon signed rank test, with a minimum of 1.4-fold change. Analysis of microarray data using the dChip analysis program yielded 32 candidate genes with both significant expression and significant change (p<0.05) between pre- and post-treatment. These genes are listed below in Table 3a.

a total reaction volume of 25 μl, containing 5 μl of diluted cDNA, 10 μl H20, 9.94 μl of the fluorescent indicator Sybrgreen® and 0.03 μl of each nucleotide primer (250 μM). PCR was carried out in a 7300 Real Time PCR System (Applied Biosystems, Foster City, Calif.), using 40 cycles of 95° C. for 15 seconds, followed by 60° C. for 1 minute, with a 10 minute 95° C. initial soak. Each measurement was made in TABLE 3a Transcripts changed in PBMC's pre- and post- antibiotic therapy.

| Gene name | probe set | fold change | p value |
| --- | --- | --- | --- |
| ADAM metallopeptidase domain 9 (meltrin gamma) | 202381_at | −2.5 | 0.004 |
| Fc fragment of IgG, high affinity Ia, receptor (CD64) | 214511_x_at | −2.4 | 0.004 |
| Kruppel-like factor 9 | 203542_s_at | −2.4 | 0.001 |
| Charcot-Leyden crystal protein | 206207_at | −2.3 | 0.018 |
| histocompatibility (minor) 13 | 232209_x_at | −2.1 | 0.014 |
| chondroitin sulfate proteoglycan 2 (versican) | 204619_s_at | −1.9 | 0.001 |
| tweety homolog 3 (*Drosophila*) | 224674_at | −1.8 | 0.019 |
| hepatocellular carcinoma-associated antigen 112 | 218345_at | −1.8 | 0.004 |
| Potassium inwardly-rectifying channel, subfamily J, member 2 | 231513_at | −1.8 | 0.014 |
| alanyl (membrane) aminopeptidase (CD13, p150) | 202888_s_at | −1.7 | 0.009 |
| CD36 antigen (thrombospondin receptor) | 228766_at | −1.7 | 0.001 |
| osteoclast-associated receptor | 1554503_a_at | −1.7 | 0.007 |
| C-type lectin domain family 4, member D | 1552772_at | −1.7 | 0.006 |
| plexin D1 | 212235_at | −1.7 | 0.005 |
| Trypsin domain containing 1 | 231422_x_at | −1.7 | 0.003 |
| CD163 antigen | 203645_s_at | −1.6 | 0.003 |
| ADP-ribosylation factor-like 11 | 1552691_at | −1.6 | 0.006 |
| toll-like receptor 2 | 204924_at | −1.6 | 0.003 |
| ST8 alpha-N-acetyl-neuraminide alpha-2,8-sialyltransferase 4 | 230836_at | −1.5 | 0.003 |
| Regulatory factor X-associated ankyrin-containing protein | 1560034_a_at | −1.5 | 0.001 |
| glucosidase, alpha; acid | 202812_at | −1.5 | 0.011 |
| J-type co-chaperone HSC20 | 223647_x_at | −1.5 | 0.026 |
| Dmx-like 2 | 212820_at | −1.5 | 0.010 |
| CCAAT/enhancer binding protein (C/EBP), alpha | 204039_at | −1.4 | 0.002 |
| BRI3 binding protein | 225716_at | −1.4 | 0.002 |
| heparanase | 219403_s_at | −1.4 | 0.017 |
| Splicing factor, arginine/serine-rich 3 | 232392_at | 1.4 | 0.057 |
| interleukin 32 | 203828_s_at | 1.4 | 0.033 |
| Formin binding protein 4 | 239469_at | 1.5 | 0.000 |
| villin 2 (ezrin) | 208621_s_at | 1.6 | 0.005 |
| dehydrogenase/reductase (SDR family) member 3 | 202481_at | 1.9 | 0.011 |
| chemokine (C-C motif) receptor 5 | 206991_s_at | 2.4 | 0.007 |

Genes listed in this table meet criteria for differential expression in a paired t-test between log transformed values of pre- and post- antibiotic circulating samples (n = 10) (p < 0.05).

Gene ontology analysis was utilized to determine biologic plausibility and the gene list was narrowed to 19 genes. The false discovery rate was computed from the gene-wise p values according to Benjamini-Hochberg.

Further, high quality PBMC microarray data from 8 normal and 6 stable CF matched controls was utilized to assess baseline transcripts of the gene signature. Relationships between CF pre- and post-antibiotic genes, normal and stable CF PBMC controls were evaluated with ANOVA, with post-hoc testing determined by Fisher's PLSD (StatView, SAS Institute Inc., Cary, N.C.). Statistical significance was assigned for p-values≦0.05.

Microarray expression data from 19 genes in the development cohort were secondarily confirmed by real-time polymerase chain reaction (RT-PCR), utilizing all sufficient remaining RNA for analysis (6 of 10 total patients had sufficient RNA from both pre- and post-therapy PBMC RNA samples). First strand cDNA was made from 1 μg total RNA using a QuantiTect Reverse Transcription Kit (Qiagen, Valencia, Calif.). Quantitative real-time PCR was performed using triplicate and expressed relative to the detection of the housekeeping gene, hypoxanthine guanine phosphoribosyl transferase (HPRT). For quantitative RT-PCR, statistics were performed in StatView (SAS, Cary, N.C.), utilizing paired t-tests, and significance at P<0.05.

Of 19 genes, 10 genes were significantly changed when measured by both methods. Table 3b lists ten genes significantly changed (p<0.05) by both microarray and quantitative RT-PCR analysis in the development cohort of CF patients. Of note, the RT-PCR validation occurred in 6 pairs of RNA samples, since the other samples did not have sufficient remaining RNA after microarray to evaluate by PCR. We designated these 10 PBMC genes, reflecting treatment of CF pulmonary exacerbations, the "CF Therapeutic signature.". The vast majority of genes (nine of ten) were downregulated after resolution of the acute pulmonary exacerbation. Only IL-32 increased transcription after treatment, suggesting suppression during the acute exacerbation, with a return to normal baseline after treatment, as indicated by transcripts in normal controls.

TABLE 3b

Classification of 10 genes in the CF therapeutic gene signature

| Gene | Description | Fold change array[a] | p values array | Fold change PCR[b] | p values PCR |
|---|---|---|---|---|---|
| Cell membrane molecules and receptors | | | | | |
| CD64 | Fcg Receptor IA | -2.4 | 0.004 | -2.1 | 0.007 |
| CD36 | collagen type 1 receptor/thrombospondin receptor | -1.7 | <0.001 | -1.6 | <0.001 |
| CD163 | hemoglobin scavenger receptor | -1.6 | 0.003 | -1.7 | 0.024 |
| TLR2 | toll-like receptor 2 | -1.6 | 0.003 | -1.7 | 0.011 |
| HCA112 | hepatocellular carcinoma-associated antigen 112 | -1.8 | 0.004 | -1.6 | 0.012 |
| PLXND1 | plexin D1 | -1.7 | 0.005 | -1.3 | 0.083 |
| Immune response | | | | | |
| IL32 | interleukin 32 | 1.4 | 0.033 | 1.4 | 0.001 |
| Matrix degradation/Extravasation | | | | | |
| HPSE | heparanase | -1.4 | 0.017 | -1.6 | 0.004 |
| ADAM9 | a disintegrin & metalloproteinase, meltrin gamma | -2.5 | 0.004 | -1.7 | 0.016 |
| CSPG2 | versican, chondroitin sulfate proteoglycan 2 | -1.9 | <0.001 | -1.9 | 0.015 |

[a]Mean fold changes depicted compare pre and post antibiotic therapy expression values from oligonucleotide arrays
P values calculated by paired t-test following log transformation.
[b]Mean fold changes depicted compare pre and post antibiotic therapy real time PCR gene expression values as copies/1000 copies housekeeping gene, hypoxanthine-phosphoribosyl transferase (HPRT). (n = 6 patients' pre and post samples from development cohort). P values calculated by paired t-test following log transformation.

Figure 2A:
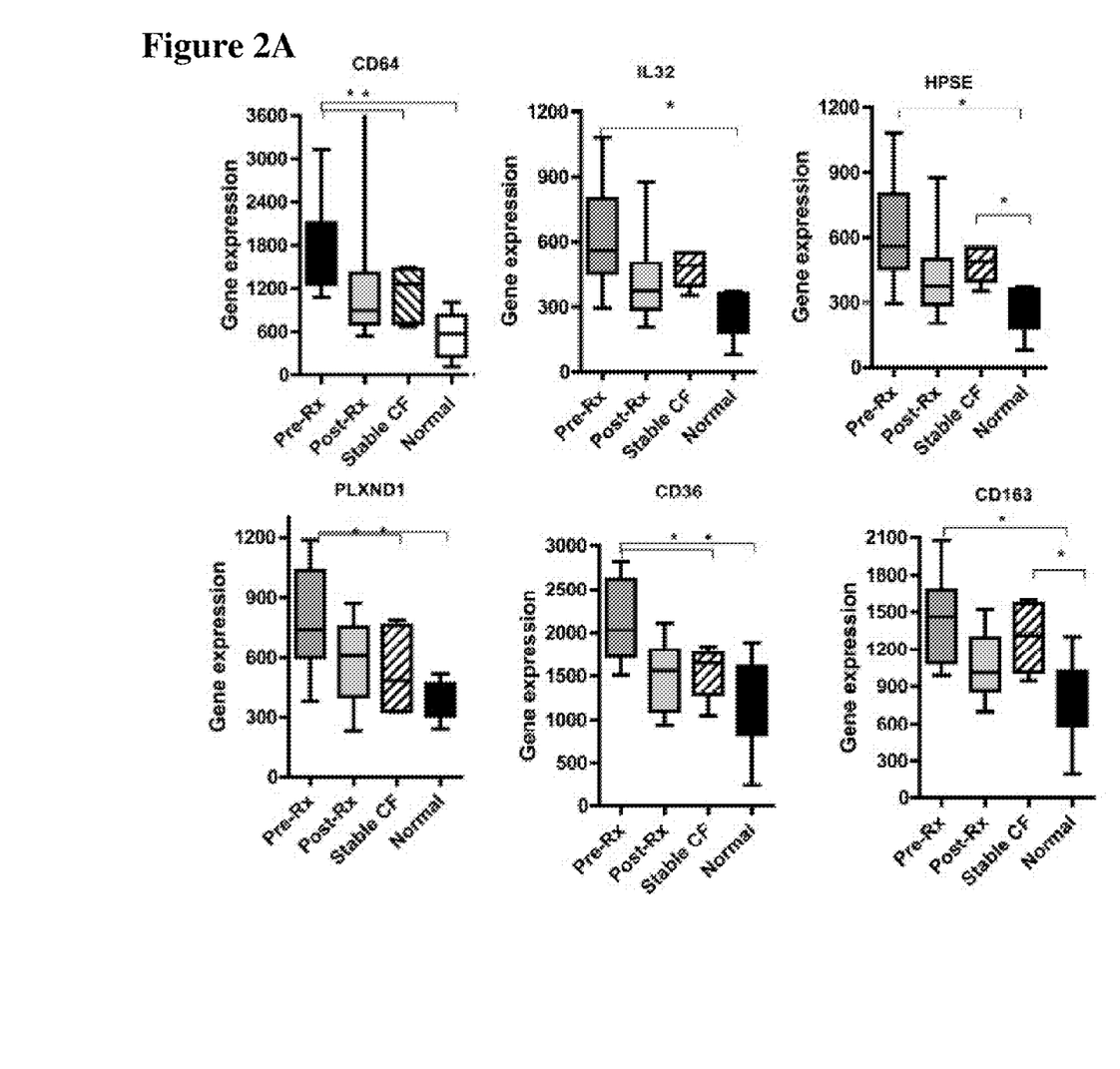
FIGS. 2A and 2B show the comparison of median expression values of the CF gene signature in pre-antibiotic (Pre-Rx) and post-antibiotic (Post-Rx) PBMC samples versus age- and gender-matched normal controls and stable CF controls. Whiskers on boxplots represent range of expression values between patient samples for each individual gene. Median is represented within each box whose boundaries represent $25^{th}$-$75^{th}$ quartiles. Differences in transcript abundance between pre- versus post-therapy CF patients were significant (p<0.05) for all genes, except for HCA112.
Figure 2B:
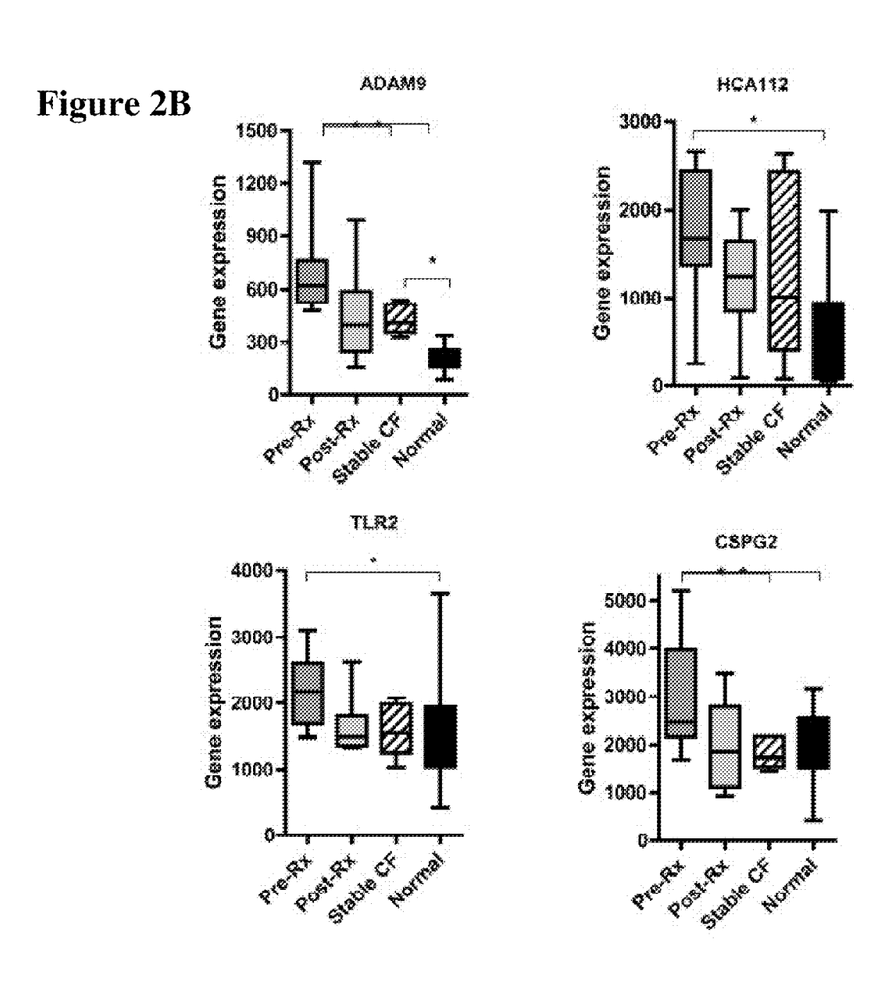

FIGS. 2A and B shows the comparison between pre- and post-antibiotic therapy median values and distribution for CF genes in the development cohort, to array data from eight age- and gender-matched normal controls, as well as six stable CF controls. Before antibiotic therapy, expression of all genes, except for TLR2, significantly differed from expression in normals (ANOVA, p<0.05; pairwise comparison with Fisher's PLSD, p<0.05) and expression of 5 of 10 genes (PLXND1, ADAM9, CSPG2, CD64 and CD36) differed from stable CF (ANOVA, p<0.05; pairwise comparison with Fisher's PLSD, p<0.05). Following treatment of the acute pulmonary exacerbation, none of the 10 genes differed significantly between post-therapy patients and stable CF controls. The following genes were significantly different between pre-antibiotic CF and stable CF and unchanged between post-antibiotic CF and stable CF: PLXND1, ADAM9, CSPG2, CD64, and CD36 (by ANOVA and pairwise comparison with Fisher's PLSD). In post-therapy CF patients, expression of three genes, CD64, ADAM9 and PLXND1, remained significantly different in CF compared to normal controls (ANOVA, p<0.05; pairwise comparison with Fisher's PLSD, p<0.05).

Figure 3:
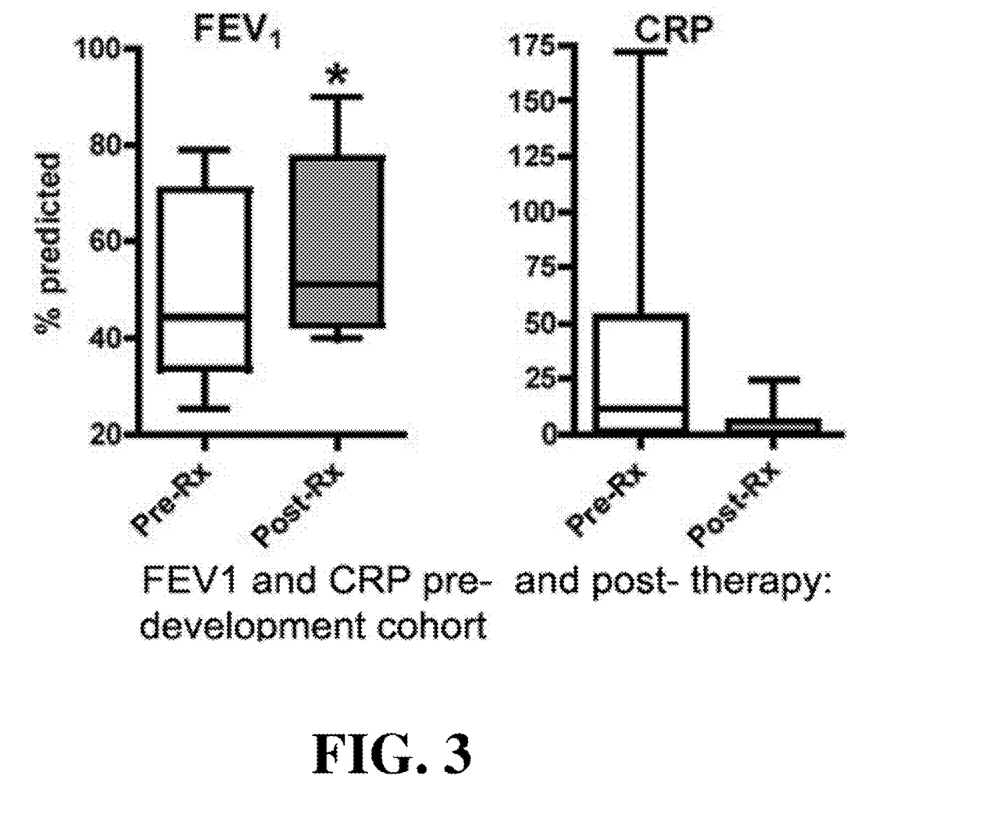
FIG. 3 shows the clinical outcomes as represented by changes in $FEV_1$% predicted and CRP pre- and post-antibiotic therapy in the development cohort. $FEV_1$ figure represents changes in $FEV_1$% predicted at initiation (Pre-Rx) and termination (Post-Rx) of antibiotics. Boxplot boundaries represent $25^{th}$-$75^{th}$ quartiles of values, with median line within box, and whiskers representing $FEV_1$% predicted ranges. CRP values in mg/dL are also depicted in pre and post therapy groups, with normal standard range. P=0.02 for differences between $FEV_1$% predicted pre and post therapy, by paired t-test. P=0.09 for differences in pre and post therapy CRP values, by paired t-test.

Associations between the ten candidate genes and common clinical outcome measures were investigated. Measurements of C-reactive protein (CRP) and FEV1 were performed simultaneously with PBMC isolation in the development cohort. CRP assays were measured utilizing nephelometry of the Dade Behring BNII. Improvement in FEV1% predicted was statistically significant after treatment, (p=0.02 by paired t test, 95% confidence intervals -1.8 to -15.78). The change in plasma CRP levels between pairs did not reach statistical significance (p=0.09). These data are shown in FIG. 3.

The correlations between gene expression values and both FEV1 and CRP levels were evaluated with Spearman's rank order correlation coefficient (rs) in Table 4 below. A significant correlation exists between the development cohort expression values and CRP values for seven of the ten genes: TLR2, CD64, CSPG2, HPSE, IL-32, CD163, and ADAM9. No correlation was noted between FEV1 change and the 10 gene CF signature.

TABLE 4

Spearman's rank correlation coefficients (rs) for genes, FEV1 and CRP pre- and post- antibiotic therapy

| | FEV1 | | CRP | |
|---|---|---|---|---|
| Variable | rs | p value | rs | p value |
| FEV1 | 1.00 | | -0.45 | 0.05* |
| CRP | -0.44 | 0.05* | 1.00 | |
| PLXND1 | -0.38 | 0.10 | 0.42 | 0.07 |
| HCA112 | 0.42 | 0.07 | 0.21 | 0.38 |
| ADAM9 | -0.35 | 0.13 | 0.57 | 0.01* |
| HPSE | 0.08 | 0.72 | 0.54 | 0.01* |
| CSPG2 | -0.31 | 0.18 | 0.45 | 0.05* |
| IL32 | 0.09 | 0.71 | -0.47 | 0.04* |
| CD64 | 0.03 | 0.88 | 0.49 | 0.03* |
| CD36 | -0.25 | 0.30 | 0.31 | 0.18 |
| CD163 | -0.42 | 0.06 | 0.48 | 0.03* |
| TLR2 | -0.18 | 0.44 | 0.49 | 0.02* |

Correlations were also conducted between the ten genes and circulating cellular markers of inflammation, namely neutrophil counts and total white blood cell counts. Results are shown in Table 5. Four genes were highly correlated (p<0.05) to circulating neutrophil counts before and after therapy: ADAM9, CSPG2, IL32, and CD163.

TABLE 5

Spearman's rank correlation coefficients (rs) for genes, PMNs and WBC pre- and post- antibiotic therapy

| | PMNS | | WBC | |
|---|---|---|---|---|
| Variable | rs | p value | rs | p value |
| PMNS | 1.00 | | 0.87 | <0.01* |
| WBC | 0.87 | <0.01* | 1.00 | |
| PLNX | 0.42 | 0.07 | 0.39 | 0.09 |
| HCA112 | -0.04 | 0.89 | -0.25 | 0.29 |
| ADAM9 | 0.47 | 0.04* | 0.28 | 0.23 |
| HPSE | 0.25 | 0.31 | -0.02 | 0.93 |
| CSPG2 | 0.54 | 0.02* | 0.31 | 0.19 |
| IL32 | -0.60 | <0.01* | -0.31 | 0.18 |
| CD64 | 0.13 | 0.61 | -0.08 | 0.75 |

TABLE 5-continued

Spearman's rank correlation coefficients (rs) for genes,
PMNs and WBC pre- and post- antibiotic therapy

| Variable | PMNS | | WBC | |
|---|---|---|---|---|
| | rs | p value | rs | p value |
| CD36 | 0.42 | 0.07 | 0.21 | 0.37 |
| CD163 | 0.50 | 0.03* | 0.36 | 0.12 |
| TLR2 | 0.24 | 0.32 | 0.21 | 0.37 |

Additionally, cytokines were measured in the aliquots of plasma taken from the same blood specimens from which PBMCs were isolated before and after antibiotic therapy. The cytokine measurements were performed as follows. Plasma collected at the time of PBMC isolation was processed at The Children's Hospital, University of Colorado GCRC Core laboratory. Multiple cytokine measurements were done using the Fluorokine® MAP Cytokine assay (R&D systems, Minneapolis, Minn.) on the Luminex 100 system (a dual laser, flow-based sorting and detection platform) to quantify the following cytokines at each blood draw: IL-1α, IL-1β, IL-IRA, IL-2, IL-4, IL-5, IL-6, IL-8, IL-10, IL-17, TNFα, IFNγ, G-CSF, GM-CSF, MIP-1β, MCP-1, VEGF, RANTES, and IL-13. All analyses were performed according to manufacturer's protocols. The mean minimal detectable doses for cytokines are as follows: IL-1α (0.39 pg/ml), IL-1β, (0.27 pg/ml), IL-1ra (2.06 pg/ml), IL-2 (0.89 pg/ml), IL-4, (1.75 pg/ml), IL-5 (0.33 pg/ml), IL-6 (0.36 pg/ml), IL-8 (0.39 pg/ml), IL-10 (0.13 pg/ml), IL-17 (0.39 pg/ml), TNF α (0.47 pg/ml), IFN γ (0.31 pg/ml), G-CSF (0.57 pg/ml), GM-CSF (1.05 pg/ml), MIP-1β (2.12 pg/ml), MCP-1 (0.95 pg/ml), VEGF (0.81 pg/ml), RANTES (1.08 pg/ml), and IL-13 (6.0 pg/ml). Univariate analysis with paired t-tests was performed to compare pre- and post-antibiotic values. The concomitant evaluation of plasma cytokines in the development cohort did not demonstrate statistical significance. Post-treatment cytokine measurements were lower than pre-treatment measurements, however, specific cytokines reduced differed from patient to patient, making none of them broadly applicable as a marker for exacerbation resolution, in a cohort of this size. Table 6 depicts mean cytokine measurements at both timepoints and associated p values. After the Bonferroni's correction for multiple tests, the change in G-CSF failed to reach significance at the p<0.05 level.

TABLE 6

CF plasma cytokine levels (mean ± SEM) pre
and post antibiotic therapy in development group

| CYTOKINE (pg/ml) | PRE-RX | POST-RX | P VALUE* |
|---|---|---|---|
| IL-1α | 0.15 ± 0.15 | <0.01 | 0.30 |
| IL-1β | 1.09 ± 0.41 | 0.88 ± 0.50 | 0.60 |
| IL-1RA | 2608 ± 1412 | 1637 ± 667 | 0.20 |
| IL-2 | 0.95 ± 0.34 | 0.45 ± 0.29 | 0.30 |
| IL-4 | <0.01 | 0.78 ± 0.40 | 0.08 |
| IL-5 | 0.93 ± 0.64 | 0.20 ± 0.11 | 0.08 |
| IL-6 | 7.34 ± 3.39 | 3.57 ± 2.03 | 0.10 |
| IL-8 | 5.37 ± 2.25 | 2.56 ± 1.31 | 0.10 |
| IL-10 | 3.24 ± 2.74 | 1.50 ± 0.55 | 0.90 |
| IL-13 | 1118 ± 388 | 1539 ± 495 | 0.30 |
| IL-17 | 2.38 ± 1.36 | 0.15 ± 0.15 | 0.08 |
| TNFα | 2.99 ± 0.83 | 3.04 ± 0.68 | 0.80 |
| IFNγ | 0.04 ± 0.04 | 0.37 ± 0.20 | 0.80 |
| G-CSF | 29.50 ± 10.30 | 12.27 ± 4.96 | 0.02 |
| GM-CSF | 0.14 ± 0.08 | 0.45 ± 0.33 | 0.06 |
| MIP-1β | 39.10 ± 13.50 | 31.51 ± 8.83 | 0.20 |
| VEGF | 10.75 ± 2.82 | 10.57 ± 2.76 | 0.50 |
| RANTES | 3216 ± 433 | 4268 ± 776 | 0.30 |

*P values calculated by paired t-test on log transformed values

The primary endpoints of the study were lung function ($FEV_1$) and gene transcript abundance changes after treatment of an acute pulmonary exacerbation. All patients were evaluated with testing as described above as well as clinical evaluation at the onset and completion of therapy. Patients who responded to therapy by manifesting improvement in $FEV_1\%$ predicted at the completion of antibiotic therapy and not requiring rehospitalization within 1 week with a diagnosis of pulmonary exacerbation were analyzed such that changes in $FEV_1\%$ predicted were regressed with transcript changes. Pulmonary function testing was performed in compliance with American Thoracic Society standards [E4]. The statistical methods used in the study were as follows. Comparison of gene expression values pre- and post-antibiotic therapy were initially performed by paired univariate analyses: t test and the Wilcoxon signed rank test.

Validation Study

Following the initial study with the Development Cohort, a validation study was performed in an independent population of CF patients made up of 14 adult CF patients suffering from an acute pulmonary exacerbation using RT-PCR.

All procedures including patient recruitment, antibiotic treatment as well as blood, microbiology, and spirometry analysis were the same as described above for the Development Cohort. PBMC isolation and FEV1 measurements were performed on adult CF patients, at the initiation and at the termination of antibiotic therapy for acute pulmonary exacerbations, using identical methods to the development cohort. This validation group of patients was heterogeneous in terms of sputum microbiology, variable use of systemic steroids, and ultimately, more representative of a realistic clinical setting. (See Table 2.)

While many patients in the Validation Cohort were treated with steroids, as opposed to none in the initial study group, the presence of steroids did not significantly alter gene expression between steroid-treated and steroid-naive patients, for nine of the ten genes (by multi-way ANOVA). Only transcript changes in HPSE significantly differed between steroid-treated and steroid naive patients (p=0.03). FEV1 improved significantly between pre- and post-measurements in this cohort (p=0.003 by paired t test). All patients in the validation cohort had a higher $FEV_1\%$ predicted at the second measurement. However, two patients in this cohort with severe airway limitation ($FEV_1$<25% predicted at both measurements) manifested ≦100 ml improvement in $FEV_1\%$ predicted and were considered non-responders based on clinical parameters. Both patients had poor outcomes: one was readmitted with recurrent pulmonary symptoms in 6 days and the second never was discharged due to persistently poor clinical response to antibiotics and underwent lung transplant 43 days later. These "non-responders" were not included in the logistic regression analysis of the validation cohort, since the model was predicated on identifying genes associated with therapeutic response.

In univariate analysis of individual gene changes within the validation cohort, five genes were significantly changed in responders after antibiotic therapy, based on log transformed gene expression values measured by RT-PCR: CD36 (p=0.002), CD64 (p=0.007), PLXND1 (p=0.01), CSPG2 (p=0.002), and TLR2 (p=0.05).

Example 3

This Example illustrates the diagnostic value of the CF therapeutic signature in association with % change in $FEV_1$ and demonstrates that the gene expression values from the CF therapeutic signature enhance the predictive discriminating value of $FEV_1$ alone.

In a multivariate analysis, the combined explanatory power of $FEV_1$ in combination with gene expression values was evaluated. Utilizing Generalized Estimating Equations, multivariate logistic regression models were constructed predicting resolution of acute pulmonary exacerbations as a function of $FEV_1$% predicted, and the discriminative value of combinations of genes identified by the development cohort (SAS, SAS Institute Inc., Cary, N.C.). An unstructured correlation structure between time points was utilized, and a stepwise selection procedure chose the most significant combination of $FEV_1$ improvement and transcript changes. $FEV_1$% predicted was forced into modeling due to its known clinical reliability, as a standard assessment for response to therapy. To identify the most frugal combination of predictors to predict resolution of inflammation, a p value <0.05 was required for entry into the model, which also allowed for determination of the unique contribution of the genes over and above $FEV_1$ alone. Finally, receiver operating characteristic (ROC) analyses reflected the overall diagnostic value of the gene markers, in terms of enhanced sensitivity and specificity over $FEV_1$ alone.

Figure 4A:
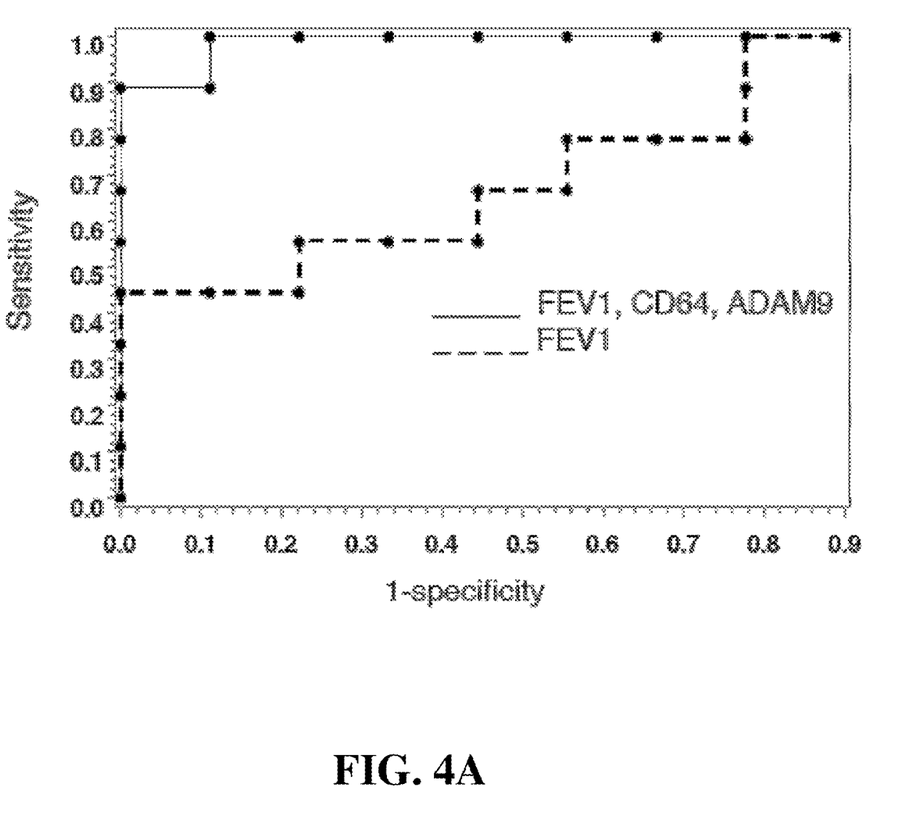
FIG. 4A shows the ROC curves for the development cohort depicting discriminatory capacity of $FEV_1$% predicted alone versus $FEV_1$ with CD64 and ADAM9 transcripts (C statistic=0.88).
Figure 4B:
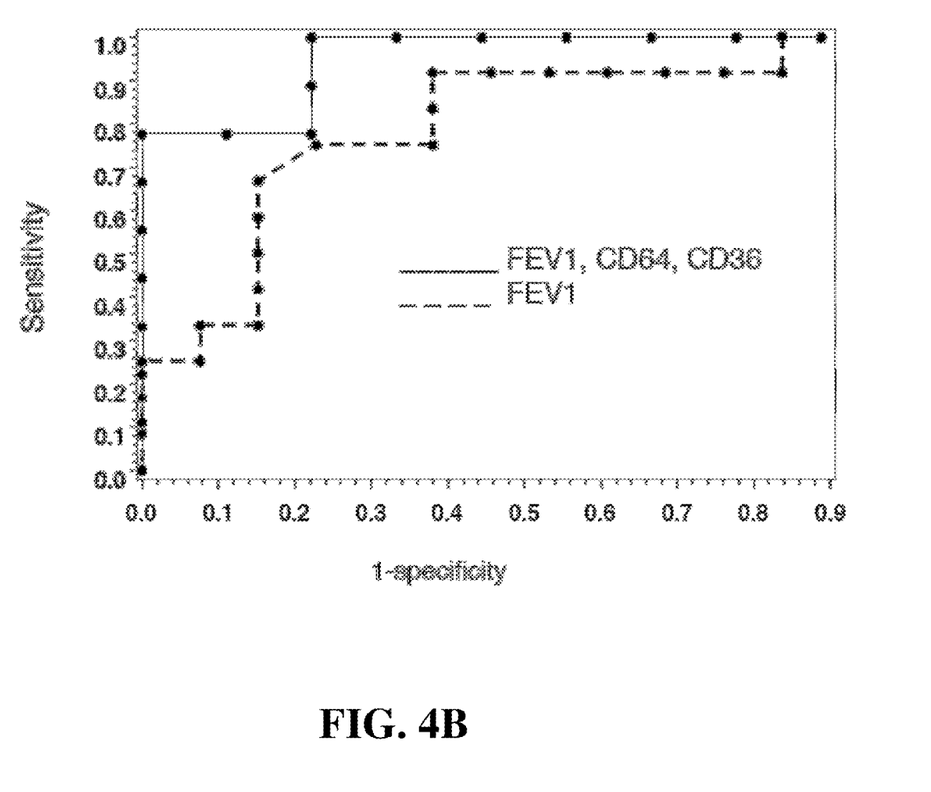
FIG. 4B shows the ROC curves for validation group comparing $FEV_1$% predicted alone to $FEV_1$ plus CD64 and CD36 transcripts (C statistic 0.80).

The addition of two gene measurements to the regression substantially increased the explanatory power of the model. As shown in FIGS. 4A and 4B, the ROC curves demonstrated the sensitivity and specificity of gene expression values for assessing treatment response. Juxtaposition of ROC curves demonstrated the additional discriminatory capacity of gene measurements in comparison to FEV1 alone, to diagnose resolution of airway inflammation.

In the development cohort, 4 different pairs of genes combined with FEV1 (C-statistic=0.75, 0.85, and 0.88 respectively) to give an overall better diagnostic performance in comparison to FEV1 alone (C-statistic=0.58). In the validation cohort, four different pairs of genes in combination with $FEV_1$ (C-statistic ranging from 0.73 to 0.80) demonstrated a more robust performance than did $FEV_1$ alone (C statistic=0.69). Table 7 demonstrates diagnostic values (area under ROC curves) for pairs of PBMC gene markers and their independent association with improvement in $FEV_1$, in both development and validation groups.

TABLE 7

Diagnostic value of CF therapeutic signature for resolution of airway inflammation

| | Markers | Area under ROC curve | p values (logistic regression) Gene 1 | Gene 2 | FEV1 |
|---|---|---|---|---|---|
| Dev. Cohort | CD64 ADAM9 | 0.88 | 0.0003 | 0.03 | 0.89 |
| | CD64 PLXND1 | 0.85 | 0.003 | 0.01 | 0.19 |
| | CSPG2 ADAM9 | 0.85 | 0.01 | 0.005 | 0.85 |

TABLE 7-continued

Diagnostic value of CF therapeutic signature for resolution of airway inflammation

| | Markers | Area under ROC curve | p values (logistic regression) Gene 1 | Gene 2 | FEV1 |
|---|---|---|---|---|---|
| | CSPG2 CD163 | 0.75 | 0.008 | 0.03 | 0.64 |
| | FEV1 alone | 0.58 | | | 0.004 |
| Valid. Cohort | CD64 CD36 | 0.8 | 0.02 | 0.03 | 0.5 |
| | CD64 CSPG2 | 0.77 | 0.02 | 0.004 | 0.6 |
| | CD64 IL32 | 0.76 | 0.03 | 0.02 | 0.5 |
| | CD36 ADAM9 | 0.73 | 0.02 | 0.03 | 0.4 |
| | FEV1 alone | 0.69 | | | 0.25 |

As demonstrated by p values <0.05 for each gene in the model, the genes contributed meaningful diagnostic information not available from $FEV_1$ alone. The use of 2 gene markers combined with $FEV_1$ was an optimal pairing, as less than two lost significance and greater than two did not improve significance by logistic function. From the 10 gene signature, 7 genes were strong independent predictors for treatment response in the regression model for the 2 groups. Three genes significantly improved diagnostic value (p≦0.05) in both cohorts. In the first cohort, the gene pair with the highest predictive accuracy, based on C statistic, as well as statistical significance for each gene in the model, consisted of CD64 and ADAM9 (C=0.88). In the validation cohort, the best predictive pair, in terms of C statistic and significance in all genes, was represented by CD64 and CD36 (C=0.80). The independent, significant explanatory power contributed by these genes to both patient groups demonstrates that gene expression values from the CF therapeutic signature enhance the predictive discriminating value of $FEV_1$ alone.

The foregoing description of the present invention has been presented for purposes of illustration. The description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Each publication and reference cited herein is incorporated herein by reference in its entirety.

The invention claimed is:
1. A method to assess response to antibiotic treatment of acute pulmonary exacerbation in a human subject having cystic fibrosis comprising:
   a) detecting the level of mRNA expression of CD64, IL32, PLXND1, HCA112, TLR2, and CD163 genes in a PBMC sample isolated from a blood sample taken from the subject before administering the treatment;
   b) detecting the level of mRNA expression of CD64, IL32, PLXND1, HCA112, TLR2, and CD163 genes in a PBMC sample isolated from a blood sample taken from the subject after administering the treatment;
   c) comparing the level of mRNA expression of the genes from step (a) in the sample taken from the subject before administering the treatment to the mRNA level of the expression of the genes from step (b) in the sample taken from the subject after administering the treatment; and d) predicting that the subject will respond to the treatment if there is a difference in the mRNA expression levels of CD64, PLXND1, HCA112, TLR2, CD163 and IL32 genes from step (a) compared to the mRNA expression levels of the same genes from step (b).

2. The method of claim 1, further comprising the step of measuring $FEV_1$ in the subject before and after administering the treatment.

3. The method of claim 1, wherein the method further comprises detecting the level of mRNA expression of one or more genes selected from the group consisting of ADAM9 and CD36 in the PBMC sample.

4. The method of claim 1, wherein the sample comprises one or more cells selected from the group consisting of: leukocytes, lymphocytes, monocytes, basophils, and eosinophils.

5. The method of claim 1, wherein detecting the level of mRNA expression comprises detection of the proteins encoded by said genes.

\* \* \* \* \*